United States Patent [19]

L'Italien

[11] 4,144,246
[45] Mar. 13, 1979

[54] PYRROLIDINEACETIC ACID ESTERS
[75] Inventor: Yvon J. L'Italien, Plymouth, Mich.
[73] Assignee: Parke, Davis & Company, Detroit, Mich.
[21] Appl. No.: 741,836
[22] Filed: Nov. 15, 1976
[51] Int. Cl.$^2$ .......................................... C07D 207/26
[52] U.S. Cl. ............................. 260/326.43; 424/274
[58] Field of Search .................................. 260/326.43
[56] References Cited
PUBLICATIONS Merck Index-9th Ed., Merck & Co., Rahway, N. J., 1976, fig. 7289.
C. F. Koelsch et al., "Synthesis of Methyl-6--phenyl-3-methyl-3-azapimelate", Journal of Organic Chemistry, vol. 21, 1956, p. 1211.
March, Advanced Organic Chemistry, 1968, p. 340.
Mindus, P. et al., Actapsychiat. Scand (1976), 54, pp. 150-160.

*Primary Examiner*—Donald G. Daus
*Assistant Examiner*—Lisa Jones
*Attorney, Agent, or Firm*—Stephen Raines; David B. Ehrlinger

[57] ABSTRACT

Lower alkyl 2-oxo-4-phenyl-1-pyrrolidineacetic acid esters which are useful as pharmacological agents, especially cognition activators, are disclosed. They can be produced by reacting 4-phenyl-2-pyrrolidinone with a lower alkyl haloacetate in the presence of a strong base.

3 Claims, No Drawings

PYRROLIDINEACETIC ACID ESTERS

SUMMARY AND DETAILED DESCRIPTION

The present invention relates to new pyrrolidineacetic acid esters. More particularly, the invention relates to new lower alkyl 2-oxo-4-phenyl-1-pyrrolidineacetic acid esters of the formula

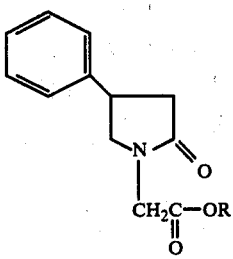

and to a method for the production of the foregoing compounds; where R is a lower alkyl group having from one to five carbon atoms, preferably being methyl.

In accordance with the invention, the foregoing compounds can be prepared by reacting 4-phenyl-2-pyrrolidinone with a lower alkyl haloacetate of the formula

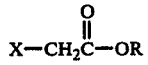

in the presence of a strong base, where R is a lower alkyl group having from one to five carbon atoms and X is chlorine, bromine or iodine. Some examples of suitable bases are alkali metals, such as sodium, alkali metal hydrides, such as potassium hydride or alkali metal amides, such as sodium amide; however, the prefered base is sodium hydride. The foregoing reaction is conducted in a solvent which may be a hydrocarbon such as benzene, toluene or xylene; an ether such as diethyl ether, dioxane, tetrahydrofuran or diethylene glycol dimethyl ether; a tertiary amide such as dimethylformamide, N,N-dimethylacetamide or 1-methyl-2-pyrrolidinone; and mixtures of these. A prefered solvent is tetrahydrofuran. While a moderate excess of any of the reactants may be employed, preferably approximately equimolar quantities of 4-phenyl-2-pyrrolidinone, base and lower alkyl haloacetate are used.

The above reaction is generally conducted at room temperature. However, since the temperature is not critical, temperatures of from about 0° C. to about 100° C. may be employed for periods of from about thirty minutes to about twenty-four hours. The more reactive esters, such as where halo is iodine, require shorter reaction periods at lower temperatures, while less reactive esters, such as where halo is chloro, require longer periods and higher temperatures. The lower alkyl 2-oxo-4-phenyl-1-pyrrolidineacetic acid esters are generally isolated and purified by distillation after evaporation of the solvent.

The starting material 4-phenyl-2-pyrrolidinone is reported in Chemical Abstracts 53:4253g. The lower alkyl haloacetates are readily available starting materials.

The compounds of the invention can exist in anhydrous form as well as in solvated, including hydrated, forms. In general, the hydrated forms and the solvated forms with pharmaceutically-acceptable solvents are equivalent to the anhydrous or unsolvated form for the purposes of the invention. In addition, they can exist in racemic form as well as in optically active d- and l-forms.

The compounds of the invention are new chemical compounds of value as pharmacological agents. More specifically, they are cognition activators which are potentially useful in treating patients suffering from senility. In addition, the alerting and attention focusing quality of these compounds would make them useful in treating patients having certain learning disabilities.

The effectiveness of the aforementioned compounds is determined by the test given below which is designed to show the compounds ability to reverse amnesia produced by an electroconvulsive shock treatment.

One hundred male mice (Carworth, CF-1 strain, 19-21 g. at time of shipment) are divided into five groups of 20 mice each. Each mouse is placed, one at a time, on a small shelf attached to the outside wall of a test box. In this position the mouse is suspended in space. Therefore, the mouse is motivated to step from the shelf through a conveniently placed small hole into the interior of the box. As soon as the mouse has all four feet within the semidarkened interior of the box, the grid floor of the box is electrified (1.5 milliamps, 3 second duration) to produce a strong pair-fear reaction from the animal. About five seconds thereafter, the mouse is removed from the test box and placed in a group holding cage.

Two hours after the above training the mice are given a single electroconvulsive shock produced by 20 milliamps delivered for 0.5 seconds through the ears. Immediately thereafter, the mice are returned to the holding cage.

Two hours after the convulsive treatment, the mice are injected intraperitoneally with the chemical being assessed. Usually three doses of the chemical will be tested at a time.

One hour after the drug treatment, the mice are tested for memory of the painful foot shock received within the shelf-box apparatus. This testing is accomplished by once again placing each mouse on the small shelf attached to the test box. Any mouse that stays on the shelf for 60 seconds without entering the box is counted as remembering the painful foot shock received within the box five hours earlier. Any mouse entering the box within the 60-second period is counted as having amnesia for the painful event.

Using this 60-second criterion, appropriate control experiments show (1.) 100 percent of mice will enter the box if no foot shock is delivered during the original training, (painful foot shock is necessary if the mice are to develop an aversion to entering the test box) (2.) 100 percent of mice will enter the box under the foregoing conditions even when treated with electroconvulsive shock at the three-hour point prior to testing (electroconvulsive shock treatment itself does not generate a fear of entering the test box).

The five groups of mice are treated as follows:

| Group | | Treatments |
|---|---|---|
| 1) | Ceiling Control Group: | Placebo |
| 2) | Base Line Control Group: | Electroconvulsive shock, Placebo |
| 3) | 1st Drug Dose Group: | Electroconvulsive shock, 2-oxo-4-phenyl-1-pyrrolidine-acetic acid, methyl ester |
| 4) | 2nd Drug Dose Group: | Electroconvulsive shock, |

| Group | Treatments |
| --- | --- |
| 5) 3rd Drug Dose Group: | 2-oxo-4-phenyl-1-pyrrolidine-acetic acid, methyl ester Electroconvulsive shock, 2-oxo-4-phenyl-1-pyrrolidine-acetic acid, methyl ester |

The percentage of amnesia reversal is determined as follows for each drug group:

percent amnesia reversal =

$$\frac{\text{Drug group} - \text{Base line control group}}{\text{Ceiling control group} - \text{Base line control group}}$$

The following criteria is used in interpreting the percent of amnesia reversal scores:

40 percent or more (active 25 to 39 percent (boarderline) and 0 to 29 percent (inactive). 2-oxo-4-phenyl-1-pyrrolidineacetic acid, methyl ester at various doses is: 0.63 mg/kg, 9 percent; 1.25 mg/kg, 27 percent; 2.5 mg/kg, 55 percent; 5 mg/kg, 50 percent; 20 mg/kg, 50 percent; 40 mg/kg, 90 percent; 80 mg/kg, 75 percent; 160 mg/kg, 50 percent.

The invention is illustrated by the following examples.

EXAMPLE 1

A total of 8.4 g. of 57% sodium hydride dispersion in mineral oil is washed successively with 200 ml. portions of toluene to remove the mineral oil. The residual sodium hydride is suspended in 600 ml. of tetrahydrofuran and the suspension is treated portionwise, with stirring, with 32.8 g. 4-phenyl-2-pyrrolidinone. Upon completion of the addition, the stirred mixture is heated in the range of 35°–65° C. from one to three hours (monitoring hydrogen evolution), followed by the dropwise addition of 21.8 g. of methyl chloroacetate. After stirring for about 16 hours at 55°–65° C. to insure completeness of reaction, the mixture is cooled and evaporated at reduced pressure. The residue is mixed with 200 ml. of water and extracted twice with 200 ml. portions of ether. The combined ether extract is dried, evaporated and fractionated at reduced pressure. 2-oxo-4-phenyl-1-pyrrolidineacetic acid, methyl ester, is obtained as an oil, b.p. 158°–159° C./0.15mm.

EXAMPLE 2

By substituting 33.4 g. of ethyl bromoacetate for the methyl chloroacetate in Example 1, there is obtained 2-oxo-4-phenyl-1-pyrrolidineacetic acid, ethyl ester.

I claim:
1. A compound of the formula

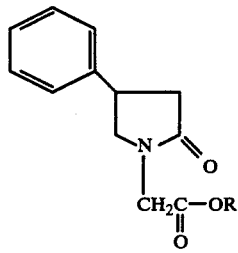

wherein R is a lower alkyl group having from one to five carbon atoms.

2. The compound of claim 1 having the name 2-oxo-4-phenyl-1-pyrrolidineacetic acid, methyl ester.

3. The compound of claim 1 having the name 2-oxo-4-phenyl-1-pyrrolidineacetic acid, ethyl ether.

* * * * *